(12) United States Patent
Flohr et al.

(10) Patent No.: US 6,841,556 B2
(45) Date of Patent: Jan. 11, 2005

(54) PYRAZOLOISOQUINOLINE DERIVATIVES FOR INHIBITING NFκB-INDUCING KINASE

(75) Inventors: Stefanie Flohr, Basel (CH); Thorsten Naumann, Hirzenhain (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 10/613,482

(22) Filed: Jul. 3, 2003

(65) Prior Publication Data

US 2004/0097541 A1 May 20, 2004

Related U.S. Application Data

(60) Provisional application No. 60/423,954, filed on Nov. 5, 2002.

(30) Foreign Application Priority Data

Jul. 3, 2002 (DE) .......................... 102 29 762

(51) Int. Cl.⁷ .................. C61K 31/44; C07D 471/00; C07D 471/02
(52) U.S. Cl. ...................... 514/293; 546/82; 546/84
(58) Field of Search ............................ 514/293; 546/82, 546/84

(56) References Cited

U.S. PATENT DOCUMENTS 4,748,246 A 5/1988 Skotnicki et al.

FOREIGN PATENT DOCUMENTS

| EP | 1134221 | 9/2001 |
|---|---|---|
| GB | 2185255 A * | 1/1987 |
| GB | 2185255 | 7/1987 |
| WO | WO 02/44153 | 6/2002 |
| WO | WO 03/024936 | 3/2003 |

OTHER PUBLICATIONS

Lucia Cecchi et al., Synthesis of 1,5–Diaryl–3–Methyl–1 H–pyrazolo[4,5–c] Isoquinolines And Studies of Binding to Specific Peripheral Benzodiazepine Binding Sites, Journal of Pharmaceutical Sciences (1989, pp. 437–442, vol. 78, No. 6).

Yumi Yamamoto et al., Role of the NF–κB Pathway in the Pathogenesis of Human Disease States, Current Molecular Medicine (2001, pp. 287–296, vol. 1).

* cited by examiner

*Primary Examiner*—D. Margaret Seaman
(74) *Attorney, Agent, or Firm*—Balaram Gupta

(57) ABSTRACT

Compounds of the formula I

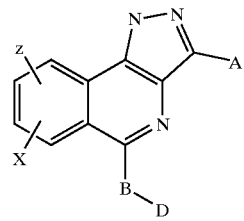

(I)

are suitable for producing pharmaceuticals for the prophylaxis and therapy of diseases whose course involves an increased activity of NIK.

15 Claims, No Drawings

PYRAZOLOISOQUINOLINE DERIVATIVES FOR INHIBITING NFκB-INDUCING KINASE

This application claims the benefit of U.S. Provisional Application No. 60/423,954, filed Nov. 5, 2002, and German Application No. 10229762.2, filed Jul. 3, 2002.

The invention relates to novel pyrazoloisoquinoline derivatives, to processes for preparing them and to their use as pharmaceuticals, in particular their use for inhibiting NFκB-inducing kinase (NIK). The pyrazoloisoquinoline derivatives can therefore be used for treating degenerative joint diseases.

NFκB is a heterodimeric transcription factor which is able to activate a large number of genes which encode, inter alia, proinflammatory cytokines such as IL-1, IL-2, TNFα or IL-6. NFκB is present in the cytosol of cells, where it is complexed with its naturally occurring inhibitor IκB. Stimulation of the cells, for example by cytokines, leads to the IκB being phosphorylated and subsequently broken down proteolytically. This proteolytic breakdown leads to the activation of NFκB, which then migrates into the nucleus of the cell, where it activates a large number of proinflammatory genes.

In diseases such as rheumatoid arthritis (in connection with inflammation), osteoarthritis or asthma, NFκB is activated beyond the normal extent. It has been demonstrated that pharmaceuticals such as glucocorticoids, salicylates or gold salts, which are used in the therapy of rheumatism, inhibit the NFκB-activating signal chain at various points or interfere directly with the transcription of the genes.

IkB kinase (IKK) has a central function in the NFkB signal transduction pathway since it mediates the phosphorylation of IkB. IKK is likewise activated by phosphorylation. The NFkB-inducing kinase (NIK) is a Ser/Thr kinase and participates in the activation of IKK. By means of overexpressing NIK in cell culture, it was possible to augment, in a stimulus-independent manner, the expression of NFkB-activated reporter genes or the expression of the NFkB-induced adhesion molecule ICAM1. NIK mediates this effect by interacting with, and phosphorylating, the IKKα sub-unit of IKK. By contrast, it was possible to inhibit the expression of an NFκB-activated reporter gene, and the IL1-induced expression of the adhesion molecule ICAM1, by overexpressing a dominant negative NIK mutant in cell culture. It was possible, by overexpressing the NIK C-terminal domain, which is responsible for interacting with IKK, to inhibit the TNFα-induced expression of an NFkB-activated reporter gene in cell culture. Pyrazoloisoquinoline derivatives which possess inhibitory activity directed against NIK are likewise able to inhibit the release of TNFα in LPS-stimulated and IL1β-stimulated human peripheral blood lymphocytes as well as the release of IL1β, TNFα and IL6 in LPS-stimulated whole human blood. Pyrazoloisoquinoline compounds possessing anti-inflammatory activity have already been described in the published document GB 2 185 255 A.

In the endeavor to obtain effective compounds for treating diseases whose course involves an increased activity of NFkB-inducing kinase, it has now been found that the pyrazoloisoquinoline derivatives according to the invention are strong and very specific inhibitors of NIK and exhibit good solubility in water.

The invention therefore relates to the compounds of the formula I

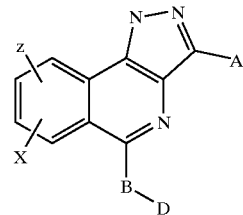

and/or a stereoisomeric form of the compound of the formula I and/or a physiologically tolerated salt of the compound of the formula I, wherein A is
1. —(C$_1$–C$_6$)-alkyl, in which alkyl is straight-chain or branched and is unsubstituted or optionally substituted, once or twice, independently of each other, by
    1.1 —O—R$^1$ or
    1.2 —C(O)—OR$^1$, in which R$^1$ is
        a) hydrogen atom or
        b) —(C$_1$–C$_6$)-alkyl,
2. —O—R$^1$,
3. —C(O)—OR$^1$, or
4. Heteroaryl having from 5 to 14 ring members, in which heteroaryl is unsubstituted or is substituted once, twice or three times, independently of each other, by R$^2$ B is
1. a covalent bond, or
2. —(C$_1$–C$_4$)-alkylene, in which alkylene is straight-chain or branched and is unsubstituted or optionally substituted, once or twice, independently of each other, by R$^1$, and R$^1$ is defined as above, D is
1. heteroaryl having from 5 to 14 ring members, in which heteroaryl is unsubstituted or is substituted once, twice or three times, independently of each other, by R$^2$, in which R$^2$ is
    a) hydrogen atom,
    b) —(C$_1$–C$_4$)-alkyl,
    c) —OH,
    d) —O—(C$_1$–C$_4$)-alkyl,
    e) halogen, or
    f) —N(R$^3$)—R$^4$, in which R$^3$ and R$^4$ are, independently of each other, hydrogen atom or —(C$_1$–C$_4$)-alkyl,
2. heterocycle having from 5 to 12 ring members, in which heterocycle is unsubstituted or substituted, once, twice or three times, independently of each other, by R$^2$, and R$^2$ is defined as above,
3. —(C$_6$–C$_{14}$)-aryl, in which aryl is unsubstituted or substituted, once, twice or three times, independently of each other, by R$^2$, and R$^2$ is defined as above, or
4. —(C$_3$–C$_6$)-cycloalkyl, in which cycloalkyl is unsubstituted or substituted, once, twice or three times, independently of each other, by R$^2$, and R$^2$ is defined as above, and X and Z are identical or different and are, independently of each other,
a) hydrogen atom,
b) —(C$_1$–C$_4$)-alkyl,
c) —OH,
d) —O—(C$_1$–C$_4$-alkyl, or
e) halogen.

The invention furthermore relates to compounds of the formula I, where

A is
1. —($C_1$–$C_3$)-alkyl, in which alkyl is straight-chain or branched and is unsubstituted or optionally substituted, once or twice, independently of each other, by
   1.1 —O—$R^1$, or
   1.2 —C(O)—O$R^1$, in which $R^1$ is
      a) hydrogen atom, or
      b) —($C_1$–$C_3$)-alkyl, or
2. —C(O)—OR1, B is a covalent bond, D is
1. phenyl, in which phenyl is unsubstituted or substituted, once, twice or three times, independently of each other, by $R^2$, in which $R^2$ is
   a) hydrogen atom,
   b) —($C_1$–$C_4$)-alkyl or,
   c) —N($R^3$)—$R^4$, in which $R^3$ and $R^4$ are, independently of each other, hydrogen atom or —($C_1$–$C_3$)-alkyl,
2. pyridyl, in which pyridyl is unsubstituted or substituted, once, twice or three times, independently of each other, by $R^2$, and $R^2$ is defined as above, or
3. —($C_4$–$C_6$)-cycloalkyl, in which cycloalkyl is unsubstituted or substituted, once, twice or three times, independently of each other, by $R^2$, and $R^2$ is defined as above, and X and Z are identical or different and are, independently of each other, hydrogen atom or halogen.

The invention furthermore relates to compounds of the formula I which are selected from the group 3,5-diphenyl-1H-pyrazolo[4,3-c]isoquinoline,
5-(3-methoxyphenyl)-3-methyl-1H-pyrazolo[4,3-c]isoquinoline,
3-(3-methyl-1H-pyrazolo[4,3-c]isoquinolin-5-yl)phenol,
5-(2-methoxyphenyl)-3-methyl-1H-pyrazolo[4,3-c]isoquinoline,
5-(2,3-dimethoxyphenyl)-3-methyl-1H-pyrazolo[4,3-c]isoquinoline,
5-(2,4-dimethoxyphenyl)-3-methyl-1H-pyrazolo[4,3-c]isoquinoline,
5-(2,6-dimethoxyphenyl)-3-methyl-1H-pyrazolo[4,3-c]isoquinoline,
5-(3,4-dimethoxyphenyl)-3-methyl-1H-pyrazolo[4,3-c]isoquinoline,
5-(3,5-dimethoxyphenyl)-3-methyl-1H-pyrazolo[4,3-c]isoquinoline,
5-(2,3,4-trimethoxyphenyl)-3-methyl-1H-pyrazolo[4,3-c]isoquinoline,
5-(2,4,6-trimethoxyphenyl)-3-methyl-1H-pyrazolo[4,3-c]isoquinoline,
5-(3,4,5-trimethoxyphenyl)-3-methyl-1H-pyrazolo[4,3-c]isoquinoline,
5-(2-ethoxyphenyl)-3-methyl-1H-pyrazolo[4,3-c]isoquinoline,
5-(4-diethylaminophenyl)-3-methyl-1H-pyrazolo[4,3-c]isoquinoline,
3-methyl-5-pyridin-4-yl-1H-pyrazolo[4,3-c]isoquinoline,
3-methyl-5-pyridin-3-yl-1H-pyrazolo[4,3-c]isoquinoline,
3-methyl-5-pyridin-2-yl-1H-pyrazolo[4,3-c]isoquinoline,
5-benzyl-3-methyl-1H-pyrazolo[4,3-c]isoquinoline,
3-methyl-5-phenethyl-1H-pyrazolo[4,3-c]isoquinoline,
3-methyl-5-(1-methylpiperidin-4-yl)-1H-pyrazolo[4,3-c]isoquinoline,
7,8-dimethoxy-3-methyl-5-phenyl-1H-pyrazolo[4,3-c]isoquinoline,
7-methoxy-3-methyl-5-phenyl-1H-pyrazolo[4,3-c]isoquinoline,
7,8-dimethxoy-5-(3-methoxyphenyl)-3-methyl-1H-pyrazolo[4,3-c]isoquinoline,
7,8-dimethoxy-3-methyl-5-pyridin-2-yl-1H-pyrazolo[4,3-c]isoquinoline,
7,8-dimethxoy-3-methyl-5-pyridin-3-yl-1H-pyrazolo[4,3-c]isoquinoline,
7-methoxy-5-(3-methoxyphenyl)-3-methyl-1H-pyrazolo[4,3-c]isoquinoline,
5-phenyl-1H-pyrazolo[4,3-c]isoquinoline-3-carboxylic acid,
Methyl 5-phenyl-1H-pyrazolo[4,3-c]isoquinoline-3-carboxylate,
(5-phenyl-1H-pyrazolo[4,3-c]isoquinolin-3-yl)methanol,
2-(3-methyl-1H-pyrazolo[4,3-c]isoquinolin-5-yl)phenol,
4-(3-methyl-1H-pyrazolo[4,3-c]isoquinolin-5-yl)benzene-2,4-diol, or
4-(3-methyl-1H-pyrazolo[4,3-c]isoquinolin-5-yl)benzene-1,2-diol.

The term "($C_1$–$C_6$)-alkyl" is understood as meaning hydrocarbon radicals whose carbon chain is straight-chain or branched and contains from 1 to 6 carbon atoms, for example methyl, ethyl, propyl, isopropyl, butyl, isobutyl, tertiary-butyl, pentyl, isopentyl, neopentyl, hexyl, 2,3-dimethylbutane or neohexyl. Examples of ($C_3$–$C_6$)-cycloalkyl radicals are compounds which are derived from 3- to 6-membered monocycles such as cyclopropyl, cyclobutyl, cyclopentyl and cyclohexyl. The term "halogen" is understood as meaning fluorine, chlorine, bromine or iodine.

The term "aryl" is understood as meaning aromatic hydrocarbon radicals having from 6 to 14 carbon atoms in the ring. Examples of ($C_6$–$C_{14}$)-aryl radicals are phenyl, naphthyl, for example 1-naphthyl and 2-naphthyl, biphenyl, for example 2-biphenyl, 3-biphenyl and 4-biphenyl, anthryl and fluorenyl. Biphenyl radicals, naphthyl radicals and, in particular, phenyl radicals are preferred aryl radicals. Aryl radicals, in particular phenyl radicals, can be substituted once or more than once, preferably once, twice or three times, by identical or different radicals, preferably by radicals from the series ($C_1$–$C_8$)-alkyl, in particular ($C_1$–$C_4$)-alkyl, ($C_1$–$C_8$)-alkoxy, in particular ($C_1$–$C_4$)-alkoxy, halogen, nitro, amino, trifluoromethyl, hydroxyl, hydroxy ($C_1$–$C_4$)-alkyl, such as hydroxymethyl or 1-hydroxyethyl or 2-hydroxyethyl, methylenedioxy, ethylenedioxy, formyl, acetyl, cyano, hydroxycarbonyl, aminocarbonyl, ($C_1$–$C_4$)-alkoxycarbonyl, phenyl, phenoxy, benzyl, benzyloxy and tetrazolyl. The same applies, in a corresponding manner, for example, for radicals such as arylalkyl or arylcarbonyl. Arylalkyl radicals are, in particular, benzyl and also 1- and 2-naphthylmethyl, 2-, 3- and 4-biphenylylmethyl and 9-fluorenylmethyl. Substituted arylalkyl radicals are, for example, benzyl radicals and naphthylmethyl radicals which are substituted, in the aryl moiety, by one or more ($C_1$–$C_8$)-alkyl radicals, in particular ($C_1$–$C_4$)-alkyl radicals, for example 2-, 3- and 4-methylbenzyl, 4-isobutylbenzyl, 4-tert-butylbenzyl, 4-octylbenzyl, 3,5-dimethylbenzyl, pentamethylbenzyl, 2-, 3-, 4-, 5-, 6-, 7- and 8-methyl-1-naphthylmethyl, and 1-, 3-, 4-, 5-, 6-, 7- and 8-methyl-2-naphthylmethyl, benzyl radicals and naphthylmethyl radicals which are substituted, in the aryl moiety, by one or more ($C_1$–$C_8$)-alkoxy radicals, in particular ($C_1$–$C_4$)-alkoxy radicals, for example 4-methoxybenzyl, 4-neopentyloxybenzyl, 3,5- dimethoxybenzyl, 3,4-methylenedioxybenzyl, 2,3,4-trimethoxybenzyl, nitrobenzyl radicals, for example 2-, 3- and 4-nitrobenzyl, halobenzyl radicals, for example 2-, 3- and 4-chlorobenzyl, 2-, 3- and 4-fluorobenzyl, 3,4-dichlorobenzyl, pentafluorobenzyl and trifluoromethylbenzyl radicals, for example 3- and 4-trifluoromethylbenzyl and 3,5-bis(trifluoromethyl)benzyl.

In monosubstituted phenyl radicals, the substituent can be located in the 2 position, the 3 position or the 4 position. Doubly substituted phenyl can be substituted in the 2,3 position, the 2,4 position, the 2,5 position, the 2,6 position, the 3,4 position or the 3,5 position. In triply substituted phenyl radicals, the substituents can be located in the 2,3,4 position, the 2,3,5 position, the 2,4,5 position, the 2,4,6 position, the 2,3,6 position or the 3,4,5 position.

The comments made with regard to the aryl radicals apply, in a corresponding manner, to divalent arylene radicals, for example to phenylene radicals, which can be present, for example, as 1,4-phenylene or as 1,3-phenylene. Phenylene-$(C_1-C_6)$-alkyl is, in particular, phenylenemethyl ($-C_6H_4-CH_2-$) and phenyleneethyl, $(C_1-C_6)$-alkylenephenyl, in particular methylenephenyl ($-CH_2-C_6H_4-$). Phenylene-$(C_2-C_6)$-alkenyl is, in particular, phenyleneethenyl and phenylenepropenyl.

The phrase "heteroaryl having from 5 to 14 ring members" means a radical of a monocyclic or polycyclic aromatic system having from 5 to 14 ring members which contains 1, 2, 3, 4 or 5 heteroatoms as ring members. Examples of heteroatoms are N, O and S. If several heteroatoms are present, they may be identical or different. Heteroaryl radicals can also be substituted, once or several times, preferably once, twice or three times, by identical or different radicals from the series $-(C_1-C_8)$-alkyl, in particular $-(C_1-C_4)$-alkyl, $-(C_1-C_8)$-alkoxy, in particular $-(C_1-C_4)$-alkoxy, halogen, nitro, $-N(R^{10})_2$, trifluoromethyl, hydroxyl, hydroxy-$(C_1-C_4)$-alkyl, such as hydroxymethyl or 1-hydroxyethyl or 2-hydroxyethyl, methylenedioxy, formyl, acetyl, cyano, hydroxycarbonyl, aminocarbonyl, $-(C_1-C_4)$-alkoxycarbonyl, phenyl, phenoxy, benzyl, benzyloxy and tetrazolyl. Heteroaryl having from 5 to 14 ring members is preferably a monocyclic or bicyclic aromatic radical which contains 1, 2, 3 or 4, in particular 1, 2 or 3, identical or different heteroatoms from the series N, O and S, and which can be substituted by 1, 2, 3 or 4, in particular 1 to 3, identical or different substituents from the series $-(C_1-C_6)$-alkyl, $-(C_1-C_6)$-alkoxy, fluorine, chlorine, nitro, $-N(R^{10})_2$, trifluoromethyl, hydroxyl, hydroxy-$(C_1-C_4)$-alkyl, $-(C_1-C_4)$-alkoxycarbonyl, phenyl, phenoxy, benzyloxy and benzyl. Particularly preferably, heteroaryl is a monocyclic or bicyclic aromatic radical having from 5 to 10 ring members, in particular a 5-membered to 6-membered monocyclic aromatic radical which contains 1, 2 or 3, in particular 1 or 2, identical or different heteroatoms from the series N, O and S and which can be substituted by 1 or 2 identical or different substituents from the series $-(C_1-C_4)$-alkyl, halogen, hydroxyl, $-N(R^{10})_2$, $-(C_1-C_4)$-alkoxy, phenyl, phenoxy, benzyloxy and benzyl.

The term "heterocycle having from 5 to 12 ring members" means a monocyclic or bicyclic 5-membered to 12-membered heterocyclic ring which is partially saturated or completely saturated. Examples of heteroatoms are N, O and S. The heterocycle is unsubstituted or substituted by identical or different substituents at one or more carbon atoms or at one or more heteroatoms. These substituents have been defined above in connection with the heteroaryl radical.

Examples of the terms "heteroaryl having from 5 to 14 ring members" and "heterocycle having from 5 to 12 ring members" are radicals such as acridinyl, azaspirodecanyl, azepinyl, azetidinyl, aziridinyl, benzimidazolyl, benzofuranyl, benzothiofuranyl, benzothiophenyl, benzoxazolyl, benzothiazolyl, benzotriazolyl, benzotetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 4,5-dihydrooxazolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, 1,2,3-oxadiazolyl, 1,2,4-oxadiazolyl, 1,2,5-oxadiazolyl, 1,3,4-oxadiazolyl, 1,2-oxathiepanyl, 1,2-oxathiolanyl, 1,4-oxazepanyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenyl, thiophenolyl, thiopyranyl, 1,2,3-triazinyl, 1,2,3-triazolyl, 1,2,3-triazolyl, 1,2,4-triazolyl, 1,2,5-triazolyl, 1,3,4-triazolyl and xanthenyl.

Preferred radicals are those derivable from benzodioxolane, benzofuran, benzothiazole, benzothiophene, benzoxazole, β-carboline, quinazoline, quinoline, quinoxaline, cinnoline, cyclohepta[b]-5-pyrrole, 4,5-dihydro-1,3-oxazole, dihydropyridine, 4,5-dihydro-1,3-thiazole, 1,3-dioxolane, furan, 3-hydroxypyrro-2,4-dione, imidazole, 2-imidazoline, imidazolidine, indazole, indole, indoline, isoquinoline, isoindole, isoindoline, isoxazolones, isothiazole, isoxazole, morpholine, oxadiazolidinedione, oxadiazolone, 1,2,3,5-oxathiadiazole 2-oxide, oxazole, 1,3-oxazolidine, 5-oxo-1,2,4-thiadiazole, perhydroazepine, perhydro-1,4-dioxane, phthalazine, piperazine, piperidine, pyrazine, pyrazole, pyridine, pyrimidine, pyrrole, pyrrolidine, pyrroline, tetrahydrofuran, 1,2,3,4-tetrahydroisoquinoline, tetrahydropyridine, 1,2,3,4-tetrahydroquinoline, tetrahydrothiophene, tetrazole, 1,3-thiazole, thiazolidine, thiomorpholine, thiophene, triazole and triazolone.

The invention furthermore relates to a process for preparing the compound of the formula I and/or a stereoiso meric form of the compound of the formula I and/or a physiologically tolerated salt of the compound of the formula I, which comprises a) reacting a compound of the formula IV

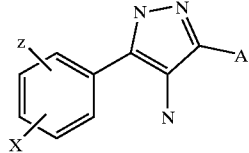

(IV)

with a compound of the formulae Va or Vb

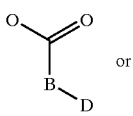

(Va)

or

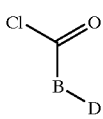

(Vb)

to give a compound of the formula VI

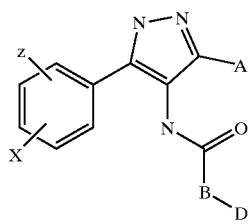

(VI)

and reacting a compound of the formula VI in the presence of phosphorus pentoxide and phosphorus oxychloride to give a protected compound of the formula I and, in conclusion, eliminating the protecting group, b) resolving a compound of the formula I, which has been prepared in accordance with method a) and which, on account of its chemical structure, appears in enantiomeric forms, into the pure enantiomers by means of salt formation with enantiomerically pure acids or bases, chromatography on chiral stationary phases or derivatization using chiral enantiomerically pure compounds, such as amino acids, separating the resulting diastereomers and eliminating the chiral auxiliary groups, or c) either isolating the compound of the formula I, which has been prepared in accordance with methods a) or b), in free form or, when acidic or basic groups are present, converting it into physiologically tolerated salts.

The starting compounds of the formula IV, Va and Vb, and reagents, which are employed can either be prepared using known methods or can be obtained commercially.

The reactions take place, for example, by reacting 3,5-substituted 1H-pyrazol-4-ylamines (compounds of the formula IV) with acids (compounds of the formula Va) in accordance with the carbodiimide method or with acid chlorides (compounds of the formula Vb) to give the corresponding amides (compounds of formula VI)

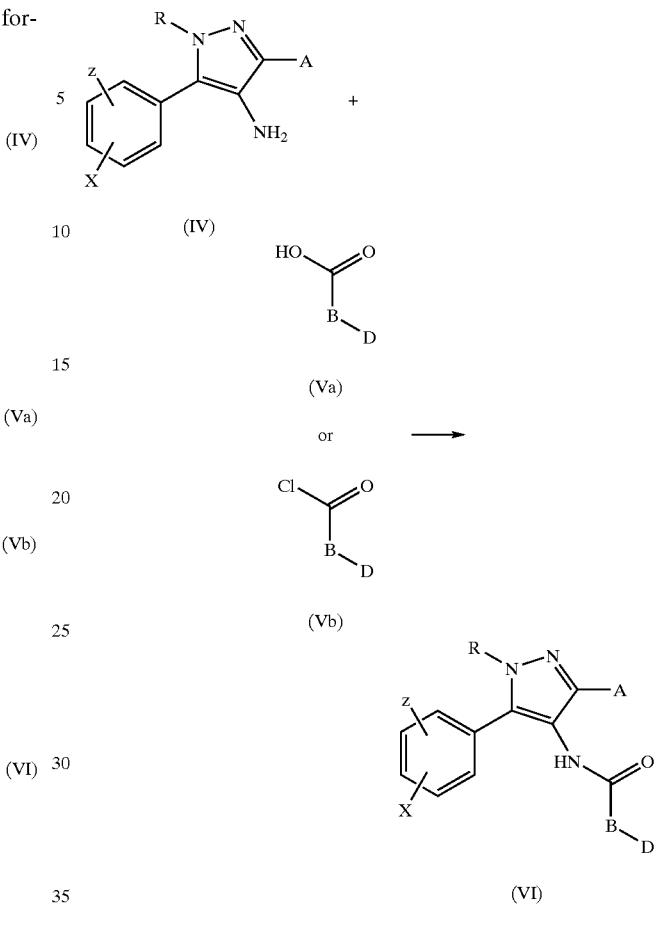

All the protected compounds of formula I can be prepared from compounds of the formula VI in the presence of phosphorus pentoxide and phosphorus oxychloride in boiling xylene. Protected compounds of the formula I are used as the starting compounds for the deprotection of functional groups and further functionalization.

If it arises in diastereoisomeric or enantiomeric form, and accrues as their mixtures in the chosen synthesis, the compound of the formula I is separated, in process step b), into the pure stereoisomers, either by chromatography on an optionally chiral support material or, if the racemic compound of the formula I is capable of salt formation, by means of fractionally crystallizing the diastereomeric salts which are formed using an optically active base or acid as auxiliary substance. Examples of suitable chiral stationary phases for the thin-layer- or column-chromatographic separation of enantiomers are modified silica gel supports (what are termed Pirkle phases) and high molecular weight carbohydrates such as triacetyl cellulose. For analytical purposes, it is also possible, after appropriate derivatization known to the skilled person, to use gas-chromatographic methods on chiral stationary phases. In order to separate the racemic carboxylic acids into the enantiomers, an optically active, as a rule commercially obtainable, base, such as (−)-nicotine, (+)- and (−)-phenylethylamine, quinine bases, L-lysine or L- and D-arginine, is used to form the differently soluble diastereomeric salts, after which the more difficultly soluble component is isolated as a solid, the more readily soluble diastereomer is separated off from the mother liquor, and the pure enantiomers are isolated from the diastereomeric salts which have been obtained in this way. It is possible, in what is in principle the same manner, to use optically active acids, such as (+)-10-camphorsulfonic acid, D- and L-tartaric acid, D- and L-lactic acid and (+)- and (−)-mandelic acid, to convert the racemic compounds of the formula I which contain a basic group, such as an amino group, into the pure enantiomers. It is also possible to use appropriately activated or optionally N-protected enantiomerically pure amino acids to convert chiral compounds which contain alcohol or amine functions into the corresponding esters or amides or, conversely, to convert chiral carboxylic acids into the amides using carboxy-protected enantiomerically pure amino acids or into the corresponding chiral esters using enantiomer pure hydroxycarboxylic acids such as lactic acid. The chirality of the amino acid or alcohol radical, which has been introduced in enantiomerically pure form, can then be used to separate the isomers by means of separating the diastereomers, which are now present, by means of crystallization or chromatography on suitable stationary phases and, after that, using suitable methods to eliminate the entrained chiral molecule moiety once again.

Acidic or basic products of the compound of the formula I can be present in the form of their salts or in free form. Preference is given to pharmacologically tolerated salts, e.g. alkali metal or alkaline earth metal salts or hydrochlorides, hydrobromides, sulfates, hemisulfates, all the possible phosphates and also salts of the amino acids, of natural bases or carboxylic acids.

Physiologically tolerated salts are prepared in a manner known per se, in accordance with process step c), from the compounds of the formula I, including their stereoisomeric forms, which are capable of salt formation. The compounds of the formula I form stable alkali metal salts, alkaline earth metal salts or optionally substituted ammonium salts with basic reagents such as hydroxides, carbonates, hydrogen carbonates, alkoxides and ammonia or organic bases, for example trimethylamine or triethylamine, ethanolamine or triethanolamine, or else basic amino acids, for example lysine, ornithine or arginine. If the compounds of the formula I possess basic groups, stable acid addition salts can also be prepared using strong acids. Both inorganic and organic acids, such as hydrochloric acid, hydrobromic acid, sulfuric acid, phosphoric acid, methanesulfonic acid, benzenesulfonic acid, p-toluenesulfonic acid, 4-bromobenzenesulfonic acid, cyclohexylamidosulfonic acid, trifluoromethylsulfonic acid, acetic acid, oxalic acid, tartaric acid, succinic acid and trifluoroacetic acid, are suitable for this purpose.

The invention also relates to a pharmaceutical which is characterized by an effective content of at least one compound of the formula I and/or of a physiologically tolerated salt of the compound of the formula I and/or an optionally stereoisomeric form of the compound of the formula I, together with a pharmaceutically suitable and physiologically tolerated carrier substance, additive and/or other active compounds and auxiliary substances.

The present invention also relates to a pharmaceutical composition, comprising at least one compound of the formula I in all its stereoisomeric forms and mixtures thereof in any ratio and/or its physiologically tolerable salts and a pharmaceutically suitable and physiologically tolerated excipient and, where appropriate, other suitable active compounds, additives or auxiliary substances.

On account of their pharmacological properties, the compounds according to the invention are suitable for producing a pharmaceutical for the selective prophylaxis and therapy of all those diseases whose course involves an increased activity of NIK.

The present invention also relates to the use of the compounds of the formula II

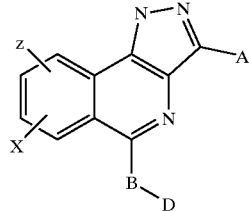

(II)

and/or a stereoisomeric form of the compound of the formula II and/or a physiologically tolerated salt of the compound of the formula II, for producing a pharmaceutical for the selective prophylaxis and therapy of all those diseases whose course involves an increased activity of NIK where A is
1. —$(C_1$–$C_6)$-alkyl, in which alkyl is straight-chain or branched and is unsubstituted or optionally substituted, once or twice, independently of each other, by
   1.1 —O—$R^1$ or
   1.2 —C(O)—$OR^1$, in which $R^1$ is
      a) hydrogen atom or
      b) —$(C_1$–$C_6)$-alkyl,
2. —O—$R^1$,
3. —C(O)—$OR^1$,
4. heteroaryl having from 5 to 14 ring members, in which heteroaryl is unsubstituted or is substituted once, twice or three times, independently of each other, by $R^2$
5. —$(C_1$–$C_6)$-alkyl, in which alkyl is straight-chain or branched, or
6. —$(C_6$–$C_{14})$-aryl, in which aryl is unsubstituted or substituted, once, twice or three times, independently of each other, by $R^2$, B is
1. a covalent bond, or
2. —$(C_1$–$C_4)$-alkylene, in which alkylene is straight-chain or branched and is unsubstituted or optionally substituted, once or twice, independently of each other, by $R^1$, and $R^1$ is defined as above, D is
1. heteroaryl having from 5 to 14 ring members, in which heteroaryl is unsubstituted or is substituted once, twice or three times, independently of each other, by $R^2$, in which $R^1$ is
   a) hydrogen atom,
   b) —$(C_1$–$C_4)$-alkyl,
   c) —OH,
   d) —O—$(C_1$–$C_4)$-alkyl,
   e) halogen, or
   f) —$N(R^3)$—$R^4$, in which $R^3$ and $R^4$ are, independently of each other, hydrogen atom or —$(C_1$–$C_4)$-alkyl,
2. heterocycle having from 5 to 12 ring members, in which heterocycle is unsubstituted or substituted, once, twice or three times, independently of each other, by $R^2$, and $R^2$ is defined as above,
3. —$(C_6$–$C_{14})$-aryl, in which aryl is unsubstituted or substituted, once, twice or three times, independently of each other, by $R^2$, and $R^2$ is defined as above, or
4. —$(C_3$–$C_6)$-cycloalkyl, in which cycloalkyl is unsubstituted or substituted, once, twice or three times, independently of each other, by $R^2$, and $R^2$ is defined as above, and X and Z are identical or different and are, independently of each other,
a) hydrogen atom,
b) —$(C_1$–$C_4)$-alkyl,
c) —OH,
d) —O—$(C_1$–$C_4$-alkyl, or
e) halogen.

The invention furthermore relates to the use of compounds of the formula II, where A is
1. —$(C_1$–$C_3)$-alkyl, in which alkyl is straight-chain or branched and is unsubstituted or optionally substituted, once or twice, independently of each other, by
1.1 —O—$R^1$, or
1.2 —C(O)—$OR^1$, in which $R^1$ is
a) hydrogen atom, or
b) —$(C_1$–$C_3)$-alkyl,
2. phenyl, or
3. —C(O)—$OR^1$, B is a covalent bond, D is
1. phenyl, in which phenyl is unsubstituted or substituted, once, twice or three times, independently of each other, by $R^2$, in which $R^2$ is
a) hydrogen atom,
b) —$(C_1$–$C_4)$-alkyl or,
c) —$N(R^3)$—$R^4$, in which $R^3$ and $R^4$ are, independently of each other, hydrogen atom or —$(C_1$–$C_3)$-alkyl,
2. pyridyl, in which pyridyl is unsubstituted or substituted, once, twice or three times, independently of each other, by $R^2$, and $R^2$ is defined as above, or
3. —$(C_4$–$C_6)$-cycloalkyl, in which cycloalkyl is unsubstituted or substituted, once, twice or three times, independently of each other, by $R^2$, and $R^2$ is defined as above, and X and Z are identical or different and are, independently of each other, hydrogen atom or halogen.

These diseases include degenerative joint diseases such as osteoarthritis and rheumatoid arthritis. The compounds of the formula II are furthermore suitable for treating asthma and transplantations such as rejection reactions on the part of the body against the transplanted organ and also rejection reactions on the part of the transplanted organ against the body into which the organ has been transplanted.

The pharmaceuticals according to the invention can be administered orally, by inhalation, rectally or transdermally or by means of subcutaneous, intraarticular, intraperitoneal or intravenous injection. Oral administration is preferred.

The invention also relates to a process for producing a pharmaceutical which comprises bringing at least one compound of the formula II, together with a pharmaceutically suitable and physiologically tolerated excipient and, where appropriate, other suitable active compounds, additives or auxiliary substances, into a suitable form for administration.

Examples of suitable solid or galenic preparation forms are granules, powders, sugar-coated tablets, tablets, (micro) capsules, suppositories, syrups, juices, suspensions, emulsions, drops or injectable solutions, and also preparations with protracted active compound release, in the preparation of which customary auxiliary substances, such as carrier substances, disintegrants, binders, coating agents, swelling agents, glidants or lubricants, flavorings, sweeteners and solubilizers are used. Frequently employed auxiliary substances which may be mentioned are magnesium carbonate, titanium dioxide, lactose, mannitol and other sugars, talc, milk protein, gelatin, starch, cellulose and its derivatives, animal and vegetable oils, such as cod liver oil, sunflower oil, groundnut oil or sesame oil, polyethylene glycol and solvents, such as sterile water and monohydric or polyhydric alcohols, such as glycerol.

The pharmaceutical preparations are preferably produced and administered in dosage units, with each unit containing as the active constituent, a particular dose of the compound of the formula II according to the invention. In the case of solid dosage units, such as tablets, capsules, sugar-coated tablets or suppositories, this dose can be up to about 1000 mg, preferably from about 50 mg to 300 mg, and, in the case of injection solutions in ampoule form, up to about 300 mg, preferably from about 10 mg to 100 mg.

Depending on the activity of the compound according to the formula II, daily doses of from about 20 mg to 1000 mg of active compound, preferably of from about 100 mg to 500 mg, are indicated for treating an adult patient of about 70 kg in weight. However, higher or lower daily doses may also possibly be appropriate. The daily dose can be administered either by means of a once-only administration in the form of a single dosage unit, or of several smaller dosage units, or by means of the multiple administration of subdivided doses at predetermined intervals.

As a rule, mass-spectroscopic methods (FAB-MS, ESI-MS) are used for determining end products, the main peak being given in each case. Temperatures are given in degrees centigrade; RT denotes room temperature (from 22° C. to 26° C.). Abbreviations which are used are either explained or correspond to the customary conventions.

The invention is explained in more detail below with the aid of examples.

PREPARATION EXAMPLES

Example 1

3,5-Diphenyl-1H-pyrazolo[4,3-c]isoquinoline (1)

a) N-(3,5-diphenyl-1H-pyrazol-4-yl)benzylamine (2)

574 mg of hydroxybenzotriazole and 822 µl of diisopropylcarbodiimide were added to a solution of 260 mg of benzoic acid in 10 ml of methylene chloride, after which 500 mg of 3,5-diphenyl-1H-pyrazol-4-ylamine in 2 ml of acetonitrile were added dropwise, at 0° C.; the mixture was then stirred at room temperature (RT) for 12 hours (h), after which water was added and the whole was extracted with ethyl acetate. The organic phase was dried over magnesium sulfate and concentrated under reduced pressure. The residue contained the title compound and was used in the following reaction without further purification.

b) 3,5-Diphenyl-1H-pyrazolo[4,3-c]isoquinoline (1)

201 mg of phosphorus pentoxide were added to a solution of 240 mg of N-(3,5-diphenyl-1H-pyrazol-4-yl)benzylamine (2) in 10 ml of xylene, after which 195 µl of phosphorus oxychloride were added dropwise at 150° C. The reaction solution was stirred at 150° C. for 4 h and then stirred at RT for 12 h; a saturated solution of sodium hydrogen carbonate was then added and the whole was extracted with methylene chloride. The organic phase was dried over magnesium sulfate, concentrated under reduced pressure and purified by means of HPLC (Merk-Hibar-Lichrospher 100-RP-18, water (0.1% trifluoroacetic acid)/acetonitrile (0.1% trifluoroacetic acid)=80/20→10/90). The following was obtained:
1. $C_{22}H_{15}N_3$ (321.38); MS (ESI) 322 (M+H)

Example 2

5-(3-Methoxyphenyl)-3-methyl-1H-pyrazolo[4,3-c]isoquinoline (3)

a) 3-Methoxy-N-(3-methyl-5-phenyl-1H-pyrazol-4-yl)benzamide (4)

311 mg of hydroxybenzotriazole and 445 µl of diisopropylcarbodiimide were added to a solution of 160 mg of 3-methoxybenzoic acid in 10 ml of dimethylformamide, after which 200 mg of 3-methyl-5-phenyl-1H-pyrazol-4-ylamine were added; the mixture was then stirred at RT for 12 h, after which water was added and the whole was extracted with methylene chloride. The organic phase was dried over magnesium sulfate, concentrated under reduced pressure and purified by means of HPLC (Merk-Hibar-Lichrospher 100-RP-18, water (0.1% trifluoroacetic acid)/acetonitrile (0.1% trifluoroacetic acid)=80/20→10/90). The following was obtained: 4 $C_{17}H_{15}N_3O_2$ (293.33); MS (ESI) 294 (M+H).

b) 5-(3-Methoxyphenyl)-3-methyl-1H-pyrazolo[4,3-c]isoquinoline (3)

128 mg of 3-methoxy-N-(3-methyl-5-phenyl-1H-pyrazol-4-yl)benzamide (4) were suspended in 5 ml of xylene and the suspension was boiled at 160° C.; 119 mg of phosphorus pentoxide were then added and the mixture was subsequently stirred at 160° C. for 15 min. 27 µl of phosphorus oxychloride were added dropwise to the suspension, which was then stirred at 160° C. for 12 h; a saturated solution of sodium hydrogen carbonate was then added and the whole was extracted with ethyl acetate. The organic phase was dried over magnesium sulfate, concentrated under reduced pressure and purified by means of HPLC (Merk-Hibar-Lichrospher 100-RP-18, water (0.1% trifluoroacetic acid)/acetonitrile (0.1% trifluoroacetic acid)=80/20→10/90). The following was obtained: 3. $C_{18}H_{15}N_3O$ (298.34); MS (ESI) 290 (M+H)

Example 3

3-(3-Methyl-1H-pyrazolo[4,3-c]isoquinolin-5-yl)phenol (5)

380 µl of 1M boron tribromide solution in methylene chloride were added dropwise, at −78° C., to a solution of 55 mg of 5-(3-methoxyphenyl)-3-methyl-1H-pyrazolo[4,3-c]isoquinoline (3) in 3 ml of methylene chloride. The reaction solution was stirred at RT for 12 h, concentrated under reduced pressure and purified by means of HPLC (Merk-Hibar-Lichrospher 100-RP-18, water (0.1% trifluoroacetic acid)/acetonitrile (0.1% trifluoroacetic acid)=80/20→10/90). The following was obtained: 5. $C_{17}H_{13}N_3O$ (275.31); MS (ESI 276 (M+H)

Example 4

5-(2-Methoxyphenyl)-3-methyl-1H-pyrazolo[4,3-c]isoquinoline (6)

a) 2-Methoxy-N-(3-methyl-5-phenyl-1H-pyrazol-4-yl)benzamide (7)

The preparation took place in analogy with Example 2a), starting with 175 mg of 2-methoxybenzoic acid. The following was obtained: 7. $C_{18}H_{17}N_3O_2$ (307.36); MS (ESI) 308 (M+H)

b) 5-(2-Methoxyphenyl)-3-methyl-1H-pyrazolo[4,3-c]isoquinoline (6)

The preparation took place in analogy with Example 1b), starting with 90 mg of 2-methoxy-N-(3-methyl-5-phenyl-1H-pyrazol-4-yl)benzamide (7). The following was obtained: 6. $C_{18}H_{15}N_3O_2$ (289.34); MS (ESI) 290 (M+H)

Example 5

5-(2,3-Dimethoxyphenyl)-3-methyl-1H-pyrazolo[4,3-c]isoquinoline (8)

a) 2,3-Dimethxoy-N-(3-methyl-5-phenyl-1H-pyrazol-4-yl)benzamide (9)

The preparation took place in analogy with Example 2a), starting with 210 mg of 2,3-dimethoxybenzoic acid. The following was obtained: 9. $C_{19}H_{19}N_3O_3$ (337.38); MS (ESI 338)(M+H)

b) 5-(2,3-Dimethoxyphenyl)-3-methyl-1H-pyrazolo[4,3-c]isoquinoline (8)

The preparation took place in analogy with Example 1b), starting with 40 mg of 2,3-dimethoxy-N-(3-methyl-5-phenyl-1H-pyrazol-4-yl)benzamide (9). The following was obtained: 8. $C_{19}H_{17}N_3O_2$ (319.37); MS (ESI) 320 (M+H)

Example 6

5-(2,4-Dimethoxyphenyl)-3-methyl-1H-pyrazolo[4,3-c]isoquinoline (10)

a) 2,4-Dimethoxy-N-(3-methyl-5-phenyl-1H-pyrazol-4-yl)benzamide (11)

The preparation took place in analogy with Example 2a), starting with 210 mg of 2,4-dimethoxybenzoic acid. The following was obtained: 11. $C_{19}H_{19}N_3O_3$ (337.38); MS (ESI) 338 (M+H)

b) 5-(2,4-Dimethoxyphenyl)-3-methyl-1H-pyrazolo[4,3-c]isoquinoline (10)

The preparation took place in analogy with Example 1b), starting with 87 mg of 2,4-dimethoxy-N-(3-methyl-5-phenyl-1H-pyrazol-4-yl)benzamide (11). The following was obtained: 10. $C_{19}H_{17}N_3O_2$ (319.37); MS (ESI) 320 (M+H)

Example 7

5-(2,6-Dimethoxyphenyl)-3-methyl-1H-pyrazolo[4,3-c]isoquinoline (12)

a) 2,6-Dimethoxy-N-(3-methyl-5-phenyl-1H-pyrazol-4-yl)benzamide (13)

The preparation took place in analogy with Example 2a), starting with 210 mg of 2,6-dimethoxybenzoic acid. The following was obtained: 13. $C_{19}H_{19}N_3O_3$ (337.38); MS (ESI) 338 (M+H)

b) 5-(2,6-Dimethoxyphenyl)-3-methyl-1H-pyrazolo[4,3-c]isoquinoline (12)

The preparation took place in analogy with Example 1b), starting with 100 mg of 2,6-dimethoxy-N-(3-methyl-5-phenyl-1H-pyrazol-4-yl)benzamide (13). The following was obtained: 12. $C_{19}H_{17}N_3O_2$ (319.37); MS (ESI 320) (M+H)

Example 8

5-(3,4-Dimethoxyphenyl)-3-methyl-1H-pyrazolo[4,3-c]isoquinoline (14)

a) 3,4-Dimethoxy-N-(3-methyl-5-phenyl-1H-pyrazol-4-yl)benzamide (15)

The preparation took place in analogy with Example 2a), starting with 210 mg of 3,4-dimethoxybenzoic acid. The following was obtained: 15. $C_{19}H_{19}N_3O_3$ (337.38); MS (ESI) 338 (M+H)

b) 5-(3,4-Dimethoxyphenyl)-3-methyl-1H-pyrazolo[4,3-c]isoquinoline (14)

The preparation took place in analogy with Example 1b), starting with 100 mg of 3,4-dimethoxy-N-(3-methyl-5-phenyl-1H-pyrazol-4-yl)benzamide (15). The following was obtained: 14. $C_{19}H_{17}N_3O_2$ (319.37); MS (ESI) 320 (M+H)

Example 9

5-(3,5-Dimethoxyphenyl)-3-methyl-1H-pyrazolo[4,3-c]isoquinoline (16)

a) 3,5-Dimethoxy-N-(3-methyl-5-phenyl-1H-pyrazol-4-yl)benzamide(17)

The preparation took place in analogy with Example 2a), starting with 210 mg of 3,5-dimethoxybenzoic acid. The following was obtained: 17. $C_{19}H_{19}N_3O_3$ (337.38); MS (ESI) 338 (M+H)

b) 5-(3,5-Dimethoxyphenyl)-3-methyl-1H-pyrazolo[4,3-c]isoquinoline (16)

The preparation took place in analogy with Example 1b), starting with 60 mg of 3,5-dimethoxy-N-(3-methyl-5-phenyl-1H-pyrazol-4-yl)benzamide (17). The following was obtained: 16. $C_{19}H_{17}N_3O_2$ (319.37); MS (ESI) 320 (M+H)

Example 10

5-(2,3,4-Trimethoxyphenyl)-3-methyl-1H-pyrazolo[4,3-c]isoquinoline (18)

a) 2,3,4-Trimethoxy-N-(3-methyl-5-phenyl-1H-pyrazol-4-yl)benzamide (19)

The preparation took place in analogy with Example 2a), starting with 244 mg of 2,3,4-trimethoxybenzoic acid. The following was obtained: 19. $C_{20}H_{21}N_3O_4$ (367.41); MS (ESI) 368 (M+H)

b) 5-(2,3,4-Trimethoxyphenyl)-3-methyl-1H-pyrazolo[4,3-c]isoquinoline (18)

The preparation took place in analogy with Example 1b), starting with 73 mg of 2,3,4-trimethoxy-N-(3-methyl-5-phenyl-1H-pyrazol-4-yl)benzamide (19). The following was obtained: 18. $C_{20}H_{19}N_3O_3$ (349.39) MS (ESI) 350 (M+H)

Example 11

5-(2,4,6-Trimethoxyphenyl)-3-methyl-1H-pyrazolo[4,3-c]isoquinoline (20)

a) 2,4,6-Trimethoxy-N-(3-methyl-5-phenyl-1H-pyrazol-4-yl)benzamide (21)

The preparation took place in analogy with Example 2a), starting with 244 mg of 2,4,6-trimethoxybenzoic acid. The following was obtained: 21. $C_{20}H_{21}N_3O_4$ (367.41); MS (ESI) 368 (M+H)

b) 5-(2,4,6-Trimethoxyphenyl)-3-methyl-1H-pyrazolo[4,3-c]isoquinoline (18)

The preparation took place in analogy with Example 1b), starting with 63 mg of 2,4,6-trimethoxy-N-(3-methyl-5-phenyl-1H-pyrazol-4-yl)benzamide (21). The following was obtained: 20. $C_{20}H_{19}N_3O_3$ (349.39); MS (ESI) 350 (M+H)

Example 12

5-(3,4,5-Trimethoxyphenyl)-3-methyl-1H-pyrazolo[4,3-c]isoquinoline (22)

a) 3,4,5-Trimethoxy-N-(3-methyl-5-phenyl-1H-pyrazol-4-yl)benzamide (23)

The preparation took place in analogy with Example 2a), starting with 244 mg of 3,4,5-trimethoxybenzoic acid. The following was obtained: 23. $C_{20}H_{21}N_3O_4$ (367.41); MS (ESI) 368 (M+H)

b) 5-(3,4,5-Trimethoxyphenyl)-3-methyl-1H-pyrazolo[4,3-c]isoquinoline (22)

The preparation took place in analogy with Example 2b), starting with 65 mg of 3,4,5-trimethoxy-N-(3-methyl-5-phenyl-1H-pyrazol-4-yl)benzamide (23). The following was obtained: 22. $C_{20}H_{19}N_3O_3$ (349.39); MS (ESI) 350 (M+H)

Example 13

5-(2-Ethoxyphenyl)-3-methyl-1H-pyrazolo[4,3-c]isoquinoline (24)

a) 2-Ethoxy-N-(3-methyl-5-phenyl-1H-pyrazol-4-yl)benzamide (25)

The preparation took place in analogy with Example 2a), starting with 191 mg of 2-ethoxybenzoic acid. The following was obtained: 25. $C_{19}H_{19}N_3O_2$ (321.389); MS (ESI) 322 (M+H)

b) 5-(2-Ethoxyphenyl)-3-methyl-1H-pyrazolo[4,3-c]isoquinoline (24)

The preparation took place in analogy with Example 1b), starting with 60 mg of 2-ethoxy-N-(3-methyl-5-phenyl-1H-pyrazol-4-yl)benzamide (25). The following was obtained: 24. $C_{19}H_{17}N_3O$ (303.37); MS (ESI) 304 (M+H)

Example 14

5-(4-Diethylaminophenyl)-3-methyl-1H-pyrazolo[4,3-c]isoquinoline (26)

a) 4-Diethylamino-N-(3-methyl-5-phenyl-1H-pyrazol-4-yl)benzamide (27)

The preparation took place in analogy with Example 2a), starting with 222 mg of 4-diethylaminobenzoic acid. The following was obtained: 27. $C_{21}H_{24}N_4O$ (348.45); MS (ESI) 349 (M+H)

b) 5-(4-Diethylaminophenyl)-3-methyl-1H-pyrazolo[4,3-c]isoquinoline (26)

The preparation took place in analogy with Example 1b), starting with 130 mg of 4-diethylamino-N-(3-methyl-5-phenyl-1H-pyrazol-4-yl)benzamide (27). The following was obtained: 26. $C_{21}H_{22}N_4$ (330.44); MS (ESI) 331 (M+H)

Example 15

3-Methyl-5-pyridin-4-yl-1H-pyrazolo[4,3-c]isoquinoline (28)

a) N-(3-Methyl-5-phenyl-1H-pyrazol-4-yl)isonicotinamide (29)

205 mg of isonicotinoyl chloride*HCl were added to a solution of 200 mg of 3-methyl-5-phenyl-1H-pyrazol-4-ylamine in 2 ml of pyridine and the mixture was then stirred at RT for 12 h; water was then added and the whole was extracted with methylene chloride. The organic phase was dried over magnesium sulfate, concentrated under reduced pressure and purified by means of HPLC (Merk-Hibar-Lichrospher 100-RP-18, water (0.1% trifluoroacetic acid)/acetonitrile (0.1% trifluoroacetic acid)=80/20→10/90). The following was obtained: 27. $C_{16}H_{14}N_4O$ (278.32); MS (ESI) 279 (M+H)

b) 3-Methyl-5-pyridin-4-yl-1H-pyrazolo[4,3-c]isoquinoline (28)

The preparation took place in analogy with Example 1b), starting with 110 mg of N-(3-methyl-5-phenyl-1H-pyrazol-4-yl)isonicotinamide (29). The following was obtained: 28. $C_{16}H_{12}N_4$ (260.30); MS (ESI) 261 (M+H)

Example 16

3-Methyl-5-pyridin-3-yl-1H-pyrazolo[4,3-c]isoquinoline (30)

a) N-(3-Methyl-5-phenyl-1H-pyrazol-4-yl)nicotinamide (31)

The preparation took place in analogy with Example 15a), starting with 205 mg of nicotinoyl chloride*HCl. The following was obtained: 31. $C_{16}H_{14}N_4O$ (278.32); MS (ESI) 279 (M+H)

b) 3-Methyl-5-pyridin-3-yl-1H-pyrazolo[4,3-c]isoquinoline (30)

The preparation took place in analogy with Example 1b), starting with 140 mg of N-(3-methyl-5-phenyl-1H-pyrazol-4-yl)nicotinamide (31). The following was obtained: 30. $C_{16}H_{12}N_4$ (260.30); MS (ESI) 261 (M+H)

Example 17

3-Methyl-5-pyridin-2-yl-1H-pyrazolo[4,3-c]isoquinoline (32)

a) N-(3-methyl-5-phenyl-1H-pyrazol-4-yl)-pyridine-2-carboxamide (33)

The preparation took place in analogy with Example 15a), starting with 205 mg of pyridine-2-carbonyl chloride*HCl. The following was obtained: 33. $C_{16}H_{14}N_4O$ (278.32); MS (ESI) 279 (M+H)

b) 3-Methyl-5-pyridin-2-yl-1H-pyrazolo[4,3-c]isoquinoline (32)

The preparation took place in analogy with Example 1b), starting with 110 mg of N-(3-methyl-5-phenyl-1H-pyrazol-4-yl)-pyridine-2-carboxamide (33). The following was obtained: 32. $C_{16}H_{12}N_4$ (260.30); MS (ESI) 261 (M+H)

Example 18

5-Benzyl-3-methyl-1H-pyrazolo[4,3-c]isoquinoline (34)

a) N-(3-Methyl-5-phenyl-1H-pyrazol-4-yl)-2-phenylacetamide (35)

The preparation took place in analogy with Example 15a), starting with 152 µl of phenylacetyl chloride. The following was obtained: 35. $C_{18}H_{17}N_3O$ (291.36); MS (ESI) 292 (M+H)

b) 5-Benzyl-3-methyl-1H-pyrazolo[4,3-c]isoquinoline (34)

The preparation took place in analogy with Example 1b), using 50 mg of N-(3-methyl-5-phenyl-1H-pyrazol-4-yl)-2-phenylacetamide (35). The following was obtained: 34. $C_{18}H_{15}N_3$ (273.34); MS (ESI) 274 (M+H)

Example 19

3-Methyl-5-phenethyl-1H-pyrazolo[4,3-c]isoquinoline (36)

a) N-(3-Methyl-5-phenyl-1H-pyrazol-4-yl)-3-phenylpropionamide (37)

The preparation took place in analogy with Example 15a), starting with 172 µl of 3-phenylpropionyl chloride. The following was obtained: 37. $C_{19}H_{19}N_3O$ (305.38); MS (ESI) 306 (M+H)

b) 3-Methyl-5-phenethyl-1H-pyrazolo[4,3-c]isoquinoline (36)

The preparation took place in analogy with Example 1b), starting with 110 mg of N-(3-methyl-5-phenyl-1H-pyrazol-4-yl)-3-phenylpropionamide (37). The following was obtained: 36. $C_{18}H_{15}N_3$ (287.37); MS (ESI) 288 (M+H)

Example 20

3-Methyl-5-(1-methylpiperidin-4-yl)-1H-pyrazolo[4,3-c]isoquinoline (38)

a) N-(3-Methyl-5-phenyl-1H-pyrazol-4-yl)-1-methylpiperidine-4-carboxamide (39)

The preparation took place in analogy with Example 2a), starting with 207 mg of 1-methylpiperidine-4-carboxylic acid*HCl and 197 µl of diisopropylethylamine. The following was obtained: 39. $C_{17}H_{22}N_4O$ (298.39); MS (ESI) 299 (M+H)

b) 3-Methyl-5-(1-methylpiperidin-4-yl)-1H-pyrazolo[4,3-c]isoquinoline (38)

The preparation took place in analogy with Example 1b), starting with 220 mg of N-(3-methyl-5-phenyl-1H-pyrazol-4-yl)-1-methylpiperidine-4-carboxamide (39). The following was obtained: 38. $C_{17}H_{20}N_4$ (280.38); MS (ESI) 281 (M+H)

Example 21

7,8-Dimethoxy-3-methyl-5-phenyl-1H-pyrazolo[4,3-c]isoquinoline (40)

a) 1-(3,4-Dimethoxyphenyl)butane-1,3-dione (41)

3.9 g of sodium hydride were initially introduced into 150 ml of cyclohexane, and a solution of 15 g of 1-(3,4-dimethoxyphenyl)ethanone in 16.3 ml of ethyl acetate was added. The reaction solution was boiled at 80° C. for 1 h, after which acetic acid was added and the whole was extracted with MTB-ether. The MTB-ether phase was dried over magnesium sulfate and subjected to rotary evaporation. The residue was chromatographed through silica gel (ethyl acetate/heptane 1/6). The following was obtained: 41 $C_{12}H_{14}O_4$ (222.24); MS (ESI) 223 (M+H)

b) 1-(3,4-Dimethoxyphenyl)butane-1,2,3-trione 2-oxime (42)

5 g of 1-(3,4-dimethoxyphenyl)butane-1,3-dione (41) were initially introduced into 25 ml of acetic acid, and 1.71 g of sodium nitrite, dissolved in 5 ml of water, were then added dropwise at 15° C. The reaction solution was stirred at RT for 1 h and then remained standing for 2 h. 50 g of ice were added to the solution and the whole was then stored at 0° C. for 12 h, in connection with which the product precipitated out. The product was subsequently filtered off with suction and dried at 50° C. in a drying oven. The following was obtained: 42 $C_{12}H_{13}NO_5$ (251.24); MS (ESI) 252 (M+H)

c) 5-(3,4-Dimethoxyphenyl)-3-methyl-4-nitro-1H-pyrazole (43)

6.77 g of 1-(3,4-dimethoxyphenyl)butane-1,2,3-trione 2-oxime (42) were dissolved in 54 ml of acetic acid, after which 0.96 g of hydrazine was added dropwise at RT and the mixture was subsequently stirred at 60° C. for 2 h. Ice was added to the reaction solution, which was then neutralized with sodium carbonate and extracted with MTB-ether. The organic phase was dried over magnesium sulfate and subjected to rotary evaporation. The following was obtained: 43. $C_{12}H_{13}N_3O_3$ (247.26); MS (ESI) 248 (M+H)

d) 5-(3,4-Dimethoxyphenyl)-3-methyl-1H-pyrazol-4-ylamine (44)

4.84 g of 5-(3,4-dimethoxyphenyl)-3-methyl-4-nitro-1H-pyrazole (43) were dissolved in 80 ml of ethanol, and 0.5 g of Pd/C was added to this solution. The solution was shaken under hydrogen for 2 h, then filtered through magnesium sulfate and subjected to rotary evaporation. The residue was chromatographed through silica gel (ethyl acetate/heptane 3/1). The following was obtained: 44 $C_{12}H_{15}N_3O_2$ (233.27); MS (ESI) 234 (M+H)

e) N-[5-(3,4-Dimethoxyphenyl)-3-methyl-1H-pyrazol-4-yl]benzamide (45)

The preparation took place in analogy with Example 15a), starting with 500 mg of 5-(3,4-dimethoxyphenyl)-3-methyl-1H-pyrazol-4-ylamine (44) and 280 µl of benzoyl chloride. The following was obtained: 45 $C_{19}H_{19}N_3O_3$ (337.38); MS (ESI) 338 (M+H)

f) 7,8-Dimethoxy-3-methyl-5-phenyl-1H-pyrazolo[4,3-c]isoquinoline (40)

The preparation place in analogy with Example 1b), starting with 187 mg of N-[5-(3,4-dimethoxyphenyl)-3- methyl-1H-pyrazol-4-yl]benzamide (45). The following was obtained: 40 $C_{19}H_7N_3O_2$ (319.37) MS (ESI) 320 (M+H)

Example 22

7-Methoxy-3-methyl-5-phenyl-1H-pyrazolo[4,3-c]isoquinoline (46)

a) 1-(4-Methoxyphenyl)butane-1,3-dione (47)

The preparation took place in analogy with Example 21a), starting with 15 g of 1-(4-methoxyphenyl)ethanone. The following was obtained: 47 $C_{11}H_{12}O_3$ (192.22); MS (ESI) 193 (M+H)

b) 1-(4-Methoxyphenyl)butane-1,2,3-trione 2-oxime (48)

The preparation took place in analogy with Example 21b), starting with 5 g of 1-(4-methoxyphenyl)butane-1,3-dione (47). The following was obtained: 48 $C_{11}H_{11}NO_4$ (221.21) MS (ESI) 222 (M+H)

c) 5-(4-Methoxyphenyl)-3-methyl-4-nitroso-1H-pyrazole (49)

The preparation took place in analogy with Example 21c), starting with 4.19 g of 1-(4-methoxyphenyl)butane-1,2,3-trione 2-oxime (48). The following was obtained: 49. $C_{11}H_{11}N_3O_2$ (217.23) MS (ESI) 218 (M+H)

d) 5-(4-Methoxyphenyl)-3-methyl-1H-pyrazol-4-ylamine (50)

The preparation took place in analogy with Example 21 d), starting with 3.17 g of 5-(4-methoxyphenyl)-3-methyl-4-nitro-1H-pyrazole (49). The following was obtained: 50. $C_{11}H_{133}N_3O$ (203.25) MS (ESI) 204 (M+H)

e) N-[5-(4-Methoxyphenyl)-3-methyl-1H-pyrazol-4-yl]benzamide (51)

The preparation took place in analogy with Example 15a), starting with 500 mg of 5-(4-methoxyphenyl)-3-methyl-1H-pyrazol-4-ylamine (50) and 315 µl of benzoyl chloride. The following was obtained: 51 $C_{18}H_{17}N_3O_2$ (307.36) MS (ESI) 308 (M+H)

f) 7-Methoxy-3-methyl-5-phenyl-1H-pyrazolo[4,3-c]isoquinoline (46)

The preparation took place in analogy with Example 1b), starting with 230 mg of N-[5-(4-methoxyphenyl)-3-methyl-1H-pyrazol-4-yl]benzamide (51). The following was obtained: 46 $C_{18}H_{15}N_3O$ (289.34) MS (ESI) 290 (M+H)

Example 23

7,8-Dimethoxy-5-(3-methoxyphenyl)-3-methyl-1H-pyrazolo-[4,3-c]isoquinoline (52)

a) N-[5-(3,4-Dimethoxyphenyl)-3-methyl-1H-pyrazol-4-yl]-3-methoxybenzamide (53)

The preparation took place in analogy with Example 15a), starting with 300 mg of 5-(3,4-dimethoxyphenyl)-3-methyl-1H-pyrazol-4-ylamine (44) and 242 mg of 3-methoxybenzoyl chloride. The following was obtained: 53 $C_{20}H_{21}N_3O_4$ (367.41) MS (ESI) 368 (M+H)

b) 7,8-Dimethoxy-5-(3-methoxyphenyl)-3-methyl-1H-pyrazolo[4,3-c]isoquinoline (52)

The preparation took place in analogy with Example 1b), starting with 291 mg of N-[5-(3,4-dimethoxyphenyl)-3-methyl-1H-pyrazol-4-yl]-3-methoxybenzamide (53). The following was obtained: 52 $C_{20}H_{19}N_3O_3$ (349.39) MS (ESI) 350 (M+H)

Example 24

7,8-Dimethoxy-3-methyl-5-pyridin-2-yl-1H-pyrazolo[4,3-c]isoquinoline (54)

a) N-[5-(3,4-Dimethoxyphenyl)-3-methyl-1H-pyrazol-4-yl]pyridine-2-carboxamide (55)

The preparation took place in analogy with Example 15a), starting with 200 mg of 5-(3,4-dimethoxyphenyl)-3-methyl-1H-pyrazol-4-ylamine (44) and 168 mg of pyridine-2-carbonyl chloride*HCl. The following was obtained: 55 $C_{18}H_{18}N_4O_3$ (338.37); MS (ESI) 339 (M+H)

b) 7,8-Dimethoxy-3-methyl-5-pyridin-2-yl-1H-pyrazolo-[4,3-c]isoquinoline (54)

The preparation took place in analogy with Example 1b), starting with 160 mg of N-[5-(3,4-dimethoxyphenyl)-3-methyl-1H-pyrazol-4-yl]pyridine-2-carboxamide (55). The following was obtained: 54 $C_{20}H_{19}N_3O_3$ (320.35) MS (ESI) 321 (M+H)

Example 25

7,8-Dimethoxy-3-methyl-5-pyridin-3-yl-1H-pyrazolo[4,3-c]isoquinoline (56)

a) N-[5-(3,4-Dimethoxyphenyl)-3-methyl-1H-pyrazol-4-yl]nicotinamide (57)

The preparation took place in analogy with Example 15a), starting with 200 mg of 5-(3,4-dimethoxyphenyl)-3-methyl-1H-pyrazol-4-ylamine (44) and 168 mg of nicotinoyl chloride*HCl. The following was obtained: 57. $C_{18}H_{18}N_4O_3$ (338.37) MS(ESI) 339 (M+H)

b) 7,8-Dimethoxy-3-methyl-5-pyridin-3-yl-1H-pyrazolo[4,3-c]isoquinoline (56)

The preparation took place in analogy with Example 1b), starting with 126 mg of N-[5-(3,4-dimethoxyphenyl)-3-methyl-1H-pyrazol-4-yl]nicotinamide (57). The following was obtained: 56 $C_{20}H_{19}N_3O_3$ (320.35) MS (ESI) 321 (M+H)

Example 26

7-Methoxy-5-(3-methoxyphenyl)-3-methyl-1H-pyrazolo-[4,3-c]isoquinoline (58)

a) 3-Methoxy-N-[5-(4-methoxyphenyl)-3-methyl-1H-pyrazol-4-yl]benzamide (59)

The preparation took place in analogy with Example 15a), starting with 300 mg of 5-(4-methoxyphenyl)-3-methyl-1H-pyrazol-4-ylamine (50) and 277 mg of 3-methoxybenzoyl chloride. The following was obtained: 59. $C_{19}H_{19}N_3O_3$ (337.38) MS (ESI) 338 (M+H)

b) 7-Methoxy-5-(3-methoxyphenyl)-3-methyl-1H-pyrazolo [4,3-c]isoquinoline (58)

The preparation took place in analogy with Example 1b), starting with 263 mg of 3-methoxy-N-[5-(4-methoxyphenyl)-3-methyl-1H-pyrazol-4-yl]benzamide (59). The following was obtained: 58 $C_{19}H_{17}N_3O_2$ (319.37) MS (ESI) 320 (M+H)

Example 27

5-Phenyl-1H-pyrazolo[4,3-c]isoquinoline-3-carboxylic acid (60)

2.1 g of potassium permanganate in 36 ml of water were added to a solution of 600 mg of 5-phenyl-3-methyl-1H-pyrazolo[4,3-c]isoquinoline in 36 ml of pyridine. The mixture was stirred at 40° C. for 12 h. The resulting suspension was filtered with suction through silica gel, after which the filtrate was concentrated under reduced pressure and the residue was purified by means of HPLC (Merk-Hibar- Lichrospher 100-RP-18, water (0.1% trifluoroacetic acid)/ acetonitrile (0.1% trifluoroacetic acid)=80/20→10/90). The following was obtained: 60. $C_{17}H_{11}N_3O_2$ (289.30) MS (ESI) 290 (M+H)

Example 28

Methyl 5-phenyl-1H-pyrazolo[4,3-c]isoquinoline-3-carboxylate (61)

18 μL of thionyl chloride were initially introduced into 0.5 ml of methanol and the mixture was stirred for 30 min. 19 mg of 5-phenyl-1H-pyrazolo[4,3-c]isoquinoline-3-carboxylic acid (60) in 0.5 ml of methanol were then added dropwise. The mixture was stirred at RT for 12 h, after which a saturated solution of sodium hydrogen carbonate was added and the whole was extracted, in each case 1×, with ethyl acetate and methylene chloride. The organic phases were combined, dried over magnesium sulfate and concentrated under reduced pressure and the residue was purified by means of HPLC (Merk-Hibar-Lichrospher 100-RP-18, water (0.1% trifluoroacetic acid)/acetonitrile (0.1% trifluoroacetic acid)=80/20→10/90). The following was obtained: 61. $C_{18}H_{13}N_3O_2$ (303.32) MS (ESI) 304 (M+H)

Example 29

(5-Phenyl-1H-pyrazolo[4,3-c]isoquinolin-3-yl)methanol (62)

7.5 mg of lithium aluminum hydride were initially introduced into 1.5 ml of tetrahydrofuran and the mixture was stirred for 10 min. 6 mg of methyl 5-phenyl-1H-pyrazolo[4,3-c]isoquinoline-3-carboxylate (61) in 1.5 ml of tetrahydrofuran were then added dropwise. The mixture was stirred at 80° C. for 3 h, after which water was added and the whole was extracted with methylene chloride. The organic phase was dried over magnesium sulfate and concentrated under reduced pressure, and the residue was purified by means of HPLC (Merk-Hibar-Lichrospher 100-RP-18, water (0.1% trifluoroacetic acid)/acetonitrile (0.1% trifluoroacetic acid)=80/20→10/90). The following was obtained: 62. $C_{17}H_{13}N_3O_1$ (275.31) MS (ESI) 276 (M+H)

Example 30

2-(3-Methyl-1H-pyrazolo[4,3-c]isoquinolin-5-yl)phenol (63)

The preparation takes place in analogy with Example 3, using 210 mg of 5-(2-methoxyphenyl)-3-methyl-1H-pyrazolo[4,3-c]isoquinoline (6). The following was obtained: 63. $C_{17}H_{13}N_3O$ (275.31) MS (ESI) 276 (M+H)

Example 31

4-(3-Methyl-1H-pyrazolo[4,3-c]isoquinolin-5-yl)benzene-2,4-diol (64)

The preparation took place in analogy with Example 3, starting with 9 mg of 5-(3,5-dimethoxyphenyl)-3-methyl-1H-pyrazolo[4,3-c]isoquinoline (16). The following was obtained: 64. $C_{17}H_{13}N_3O_2$ (291.31); MS (ESI) 292 (M+H)

Example 32

4-(3-Methyl-1H-pyrazolo[4,3-c]isoquinolin-5-yl)benzene-1,2-diol (65)

The preparation took place in analogy with Example 3, starting with 40 mg of 5-(2,3-dimethoxyphenyl)-3-methyl-1H-pyrazolo[4,3-c]isoquinoline (8). The following was obtained: 65. $C_{17}H_{13}N_3O_2$ (291.31); MS (ESI) 292 (M+H)

Pharmacological Examples

The pyrazoloisoquinoline derivatives according to the invention were tested for inhibitory activity against NIK in various in vitro assay systems. In this connection, human peripheral blood lymphocytes were preincubated for 1 h with different concentrations of the compounds and then stimulated for 24 h with LPS or IL1β. After that, a commercially obtainable ELISA test kit was used to measure the release of TNFα in the culture supernatant, and the IC50 for the given compound was determined. The cytotoxicity was measured by way of LDH release using a commercially obtainable test kit and the LD50 for the given compound was determined.

In another assay, heparinized whole human blood was preincubated for 1 h with different concentrations of the compounds and then stimulated with LPS for 24 h. Commercially available test kits were used to measure the release of IL1β, TNFα and IL6 in the supernatant after 24 h, and the IC50 for the given compound was determined.

The results are shown in the following tables 1, 2 and 3.

TABLE 1

Inhibition of TNFα release in LPS-stimulated human peripheral blood lymphocytes:

| Example No. | TNFα release IC50 (μM) | IL6 release IC50 (μM) | Cytotoxicity LD50 (μM) |
| --- | --- | --- | --- |
| 1 | 1.9 | 80 | >100 |
| 2 | 9 | >100 | >100 |
| 3 | 7.5 | 80 | >100 |

The sign ">" denotes greater than

TABLE 2

Inhibition of TNFα release in IL1β-stimulated human peripheral blood lymphocytes:

| Example No. | TNFα release IC50 (μM) | IL6 release IC50 (μM) | Cytotoxicity LD50 (μM) |
| --- | --- | --- | --- |
| 1 | 5 | 80 | >100 |
| 2 | 35 | >100 | >100 |
| 3 | 8 | >100 | >100 |

TABLE 3

Inhibition of the release of IL1β, TNFα and IL6 in LPS-stimulated heparinized whole human blood:

| Example No. | IL1β release IC50 (μM) | TNFα release IC50 (μM) | IL6 release IC50 (μM) |
| --- | --- | --- | --- |
| 1 | 33 | 12.5 | >100 |
| 2 | 1.3 | 1.2 | 7 |
| 3 | 29 | 5 | >100 |

What is claimed is:

1. A compound of the formula I

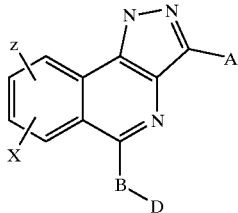

or a stereoisomeric form or a pharmaceutically acceptable salt of the compound of the formula I, wherein A is —($C_1$–$C_6$)-alkyl, in which alkyl is straight-chain or branched and is unsubstituted or optionally substituted, once or twice, independently of each other, by
  —O—$R^1$ or
  —C(O)—$OR^1$, in which $R^1$ is
    hydrogen atom or
    —($C_1$–$C_6$)-alkyl,
  —O—R1,
  —C(O)—OR1, or
  heteroaryl having from 5 to 14 ring members, in which heteroaryl is unsubstituted or is substituted once, twice or three times, independently of each other, by $R^2$, B is a covalent bond, or
  —($C_1$–$C_4$)-alkylene, in which alkylene is straight-chain or branched and is unsubstituted or optionally substituted, once or twice, independently of each other, by $R^1$, and $R^1$ is defined as above, D is heteroaryl having from 5 to 14 ring members, in which heteroaryl is unsubstituted or is substituted once, twice or three times, independently of each other, by $R^2$, in which $R^2$ is
  hydrogen atom,
  —($C_1$–$C_4$)-alkyl,
  —OH,
  —O—($C_1$_$C_4$)-alkyl,
  halogen, or
  —N($R^3$)—$R^4$, in which $R^3$ and $R^4$ are, independently of each other, hydrogen atom or —($C_1$–$C_4$)-alkyl,
  heterocycle having from 5 to 12 ring members, in which heterocycle is unsubstituted or substituted, once, twice or three times, independently of each other, by $R^2$, and $R^2$ is defined as above,
  —($C_6$–$C_{14}$)-aryl, in which aryl is substituted, once, twice or three times, independently of each other, by
  —OH
  —O—($C_1$–$C_4$)-alkyl, or
  —N($R^3$)—$R^4$, in which $R^3$ and $R^4$ are, independently of each other, hydrogen atom or —($C_1$–$C_4$)-alkyl, or
  —($C_3$–$C_6$)-cycloalkyl, in which cycloalkyl is substituted, once, twice or three times, independently of each other, by
  —($C_1$–$C_4$)-alkyl,
  —OH,
  —O—($C_1$_$C_4$)-alkyl,
  halogen, or
  —N($R^3$)—$R^4$, in which $R^3$ and $R^4$ are, independently of each other, hydrogen atom or —($C_1$–$C_4$)-alkyl, and X and Z are identical or different and are, independently of each other, hydrogen atom,
—($C_1$–$C_4$)-alkyl,
—OH,
—O—($C_1$–$C_4$-alkyl, or
halogen.

2. The compound of the formula I as claimed in claim 1, wherein

A is —($C_1$–$C_3$)-alkyl, in which alkyl is straight-chain or branched and is unsubstituted or optionally substituted, once or twice, independently of each other, by
  —O—$R^1$, or
  —C(O)—$OR^1$, in which $R^1$ is
    hydrogen atom, or
    —($C_1$–$C_3$)-alkyl, or
  —C(O)—$OR^1$, B is a covalent bond, D is phenyl, in which phenyl is substituted, once, twice or three times, independently of each other, by
  —OH,
  —O—($C_1$–$C_4$)-alkyl, or
  —N($R^3$)—$R^4$, in which $R^3$ and $R^4$ are, independently of each other, hydrogen atom or
  —($C_1$–$C_3$)-alkyl,
  pyridyl, in which pyridyl is unsubstituted or substituted, once, twice or three times, independently of each other, by $R^2$, and $R^2$ is defined as above, or
  —($C_4$–$C_6$)-cycloalkyl, in which cycloalkyl is substituted, once, twice or three times, independently of each other, by
  —($C_1$–$C_3$)-alkyl,
  —OH,
  —O—($C_1$–$C_3$)-alkyl,
  halogen, or
  —N($R^3$)—$R^4$, in which $R^3$ and $R^4$ are, independently of each other, hydrogen atom or —($C_1$–$C_3$)-alkyl, and X and Z are identical or different and are independently of each other, hydrogen atom or halogen.

3. The compound of the formula 1 as claimed in claim 1, wherein the compound of the formula I is selected from the group consisting of:

5-(3-methoxyphenyl)-3-methyl-1H-pyrazolo[4,3-c]isoquinoline,
3-(3-methyl-1H-pyrazolo[4,3-O]isoquinolin-5-yl)phenol,
5-(2-methoxyphenyl)-3-methyl-1H-pyrazolo[4,3-c]isoquinolino,
5-(2,3-dimethoxyphenyl)-3-methyl-1H-pyrazolo[4,3-c]isoquinoline,
5-(2,4-dimethoxyphenyl)-3-methyl-1H-pyrazalo[4,3-c]isoquinoline,
5-(2,6-dimethoxyphenyl)-3-methyl-1H-pyrazolo[4,3-c]isoquinoline,
5-(3,4-dimethoxyphenyl)-3-methyl-1H-pyrazolo[4,3-c]isoquinoline,
5-(3,5-dimethoxyphenyl)-3-methyl-1H-pyrazolo[4,3-c]isoquinoline,
5-(2,3,4-trimethoxyphenyl)-3-methyl-1H-pyrazolo[4,3-c]isoquinoline,
5-(2,4,6-trimethoxyphenyl)-3-methyl-1H-pyrazolo[4,3-c]isoquinoline,
5-(3,4,5-trimethoxyphenyl)-3-methyl-1H-pyrazolo[4,3-c]isoquinoline,
5-(2-ethoxyphenyl)-3-methyl-1H-pyrazolo[4,3-O]isoquinoline,
5-(4-diethylaminophenyl)-3-methyl-1H-pyrazolo[4,3-c]isoquinoline, 3-methyl-5-pyridin-4-yl-1H-pyrazolo[4,3-c]isoquinoline,
3-methyl-5-pyridin-3-yl-1H-pyrazolo[4,3-c]isoquinoline,
3-methyl-5-pyridin-2-yl-1H-pyrazolo[4,3-c]isoquinoline,
3-methyl-5-(1-methylpiperidin-4-yl)-1H-pyrazolo[4,3-c]isoquinoline,
7,8-dimethoxy-5-(3-methoxyphenyl)-3-methyl-1H-pyrazolo[4,3-c]isoquinoline,
7,8-dimethoxy-3-methyl-5-pyridin-2-yl-1H-pyrazolo[4,3-c]isoquinoline,
7,8-dimethxoy-3-methyl-5-pyridin-3-yl-1H-pyrazolo[4,8-c]isoquinoline,
7-methoxy-5-(3-methoxyphenyl)-3-methyl-1H-pyrazolo[4,3c]isoquinoline,
2-(3-methyl-1H-pyrazolo[4,3-c]isoquinolin-5-yl)phenol,
4-(3-methyl-1H-pyrazolo[4,3-c]isoquinolin-5-yl)benzene-2,4-diol, and
4-(3-methyl-1H-pyrazolo[4,3-c]isoquinolin-5-yl)benzene-1,2-diol.

4. A process for preparing a compound of the formula I as claimed in claim 1, which comprises
a) reacting a compound of the formula IV

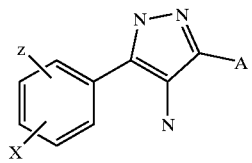

(IV)

with a compound of the formulae Va or Vb

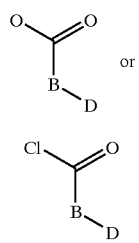

(Va)

or (Vb)

to give a compound of the formula VI

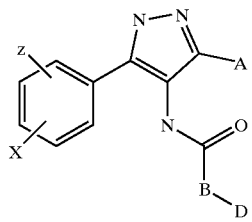

(VI)

and reacting a compound of the formula VI in the presence of phosphorus pentoxide and phosphorus oxychloride to give a protected compound of the formula I and, removing the protecting group,
b) resolving the compound of the formula I prepared in accordance with step a) and which, on account of its chemical structure, appears in enantiomeric forms, into the pure enantiomers by means of salt formation with enantiomerically pure acids or bases, chromatography on chiral stationary phases or derivatization using chiral enantiomerically pure compounds, such as amino acids, separating the resulting diastereomers and eliminating the chiral auxiliary groups, and
c) either isolating the compound of the formula I prepared in accordance with steps a) or b), in free form or, when acidic or basic groups are present, converting it into pharmaceutically acceptable salts.

5. A pharmaceutical composition comprising a therapeutically effective content of at least one compound of the formula I as claimed in claim 1 together with a pharmaceutically suitable carrier optionally in combination with a suitable additive, other motive compounds and auxiliary substances.

6. A method of treating a disease condition selected from the group consisting of osteoarthritis, rheumatoid arthritis, asthma, rejection reactions on the part of the body against a transplanted organ or rejection reactions on the part of the transplanted organ against the body, comprising administering to a patient suffering from said disease condition a therapeutically effective amount of a compound of the formula I

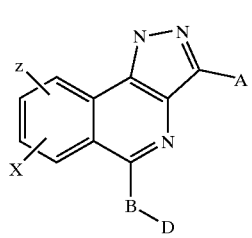

(I)

or a stereoisomeric form or a pharmaceutically acceptable salt of said compound of the formula I, optionally in combination with a pharmaceutically acceptable carrier, wherein A is —($C_1$–$C_6$)-alkyl, in which alkyl is straight-chain or branched and is optionally substituted, once or twice, independently of each other, by
—O—$R^1$ or
—C(O)—$OR^1$, in which $R^1$ is
  hydrogen atom or
  —($C_1$–$C_6$)-alkyl,
—O—R1,
—C(O)—OR1,
heteroaryl having from 5 to 14 ring members, in which heteroaryl is unsubstituted or is substituted once, twice or three times, independently of each other, by $R^2$, or
—($C_6$–$C_{14}$)-aryl, in which aryl is unsubstituted or substituted, once, twice or three times, independently of each other, by $R^2$, B is a covalent bond, or
—($C_1$–$C_4$)-alkylene, in which alkylene is straight-chain or branched and is substituted, once or twice, independently of each other, by $R^1$, and $R^1$ is defined as above.

D is heteroaryl having from 5 to 14 ring members, in which heteroaryl is unsubstituted or is substituted once, twice or three times, independently of each other, by $R^2$,
in which $R^2$ is
  hydrogen atom, —($C_1$–$C_4$)-alkyl,
  —OH,
  —O—($C_1$–$C_4$)-alkyl,
  halogen, or
  —N($R^3$)—$R^4$, in which $R^3$ and $R^4$ are, independently of each other, hydrogen atom or
—($C_1$–$C_4$)—alkyl,
heterocycle having from 5 to 12 ring members, in which heterocycle, is unsubstituted or substituted, once, twice or three times, independently of each other, by $R^2$, and $R^2$ is defined as above,
—($C_6$–$C_{14}$)-aryl, in which aryl is unsubstituted or substituted once, twice or three times, independently of each other, by $R^2$, and $R^2$ is defined as above, or
—($C_3$–$C_6$)-cycloalkyl, in which cycloalkyl is unsubstituted or substituted, once twice or three times, independently of each other, by $R^2$, and $R^2$ is defined as above, and X and Z are identical or different and are, independently of each other,
hydrogen atom,
—($C_1$–$C_4$-alkyl,
—OH,
—O—($C_1$–$C_4$-alkyl, or halogen.

7. The method as claimed in claim 6, wherein
A is —($C_1$–$C_3$)-alkyl, in which alkyl is straight-chain or branched and is unsubstituted or optionally substituted, once or twice, independently of each other, by
—O—$R^1$, or
—C(O)—$OR^1$, in which $R^1$ is
hydrogen atom, or
—($C_1$–$C_3$)-alkyl,
phenyl, or
—C(O)—$OR^1$,
B is a covalent bond,
D is phenyl, in which phenyl is unsubstituted or substituted, once, twice or three times, independently of each other, by $R^2$,
in which $R^2$ is
hydrogen atom,
—($C_1$–$C_4$)-alkyl or,
—N($R^3$)—$R^4$, in which $R^3$ and $R^4$ are,
independently of each other, hydrogen atom or —($C_1$–$C_3$)-alkyl, pyridyl, in which pyridyl is unsubstituted or substituted, once, twice or three times, independently of each other, by $R^2$, and $R^2$ is defined as above, or
—($C_4$–$C_6$)cycloalkyl, in which cycloalkyl is unsubstituted or substituted, once, twice or three times, independently of each other, by $R^2$, and $R^2$ defined as above, and X and Z are identical or different and are, independently of each other, hydrogen atom or halogen.

8. The method as claimed in claim 6 wherein said compound is selected from the group consisting of:

3,5-diphenyl-1H-pyrazolo[4,3-c]isoquinoline,
5-(3-methoxyphenyl)-3-methyl-1H-pyrazolo[4,3-c]isoquinoline,
3-(3-methyl-1H-pyrazolo[4,3-c]isoquinolin-5-yl)phenol,
5-(2-methoxyphenyl)-3-methyl-1H-pyrazolo[4,3-c]isoquinoline,
5-(2,3-dimethoxyphenyl)-3-methyl-1H-pyrazolo[4,3-c]isoquinoline,
5-(2,4-dimethoxyphenyl)-3-methyl-1H-pyrazolo[4,3-c]isoquinoline,
5-(2,6-dimethoxyphenyl)-3-methyl-1H-pyrazolo[4,3-c]isoquinoline,
5-(3,4-dimethoxyphenyl)-3-methyl-1H-pyrazolo[4,3-c]isoquinoline,
5-(3,5-dimethoxyphenyl)-3-methyl-1H-pyrazolo[4,3-c]isoquinoline,
5-(2,3,4-trimethoxyphenyl)-3-methyl-1H-pyrazolo[4,3-c]isoquinoline,
5-(2,4,6-trimethoxyphenyl)-3-methyl-1H-pyrazolo[4,3-c]isoquinoline,
5-(3,4,5-trimethoxyphenyl)-3-methyl-1H-pyrazolo[4,3-c]isoquinoline,
5-(2-ethoxyphenyl)-3-methyl-1H-pyrazolo[4,3-c]isoquinoline,
5-(4-diethylaminophenyl)-3-methyl-1H-pyrazolo[4,3-c]isoquinoline,
3-methyl-5-pyridin-4-yl-1H-pyrazolo[4,3-c]isoquinoline,
3-methyl-5-pyridin-3-yl-1H-pyrazolo[4,3-c]isoquinoline,
3-methyl-5-pyridin-2-yl-1H-pyrazolo[4,3-c]isoquinoline,
5-benzyl-3-methyl-1H-pyrazolo[4,3-c]isoquinoline,
3-methyl-5-phenethyl-1H-pyrazolo[4,3-c]isoquinoline,
3-methyl-5-(1-methylpiperidin-4-yl)-1H-pyrazolo[4,3-c]isoquinoline,
7,8-dimethoxy-3-methyl-5-phenyl-1H-pyrazolo[4,3-c]isoquinoline,
7-methoxy-3-methyl-5-phenyl-1H-pyrazolo[4,3-c]isoquinoline,
7,8-dimethoxy-5-(3-methoxyphenyl)-3-methyl-1H-pyrazolo[4,3-c]isoquinoline,
7,8-dimethoxy-3-methyl-5-pyridin-2-yl-1H-pyrazolo[4,3-c]isoquinoline,
7,8-dimethoxy-3-methyl-5-pyridin-3-yl-1H-pyrazolo[4,3-c]isoquinoline,
7-methoxy-5-(3-methoxyphenyl)-3-methyl-1H-pyrazolo[4,3-c]isoquinoline,
5-phenyl-1H-pyrazolo[4,3-c]isoquinoline-3-carboxylic acid,
methyl 5-phenyl-1H-pyrazolo[4,3-c]isoquinoline-3-carboxylate,
(5-phenyl-1H-pyrazolo[4,3c]isoquinoline-3)methanol,
2-(3-methyl-1H-pyrazolo[4,3-c]isoquinoline-5-yl)phenol,
4-(3-methyl-1H-pyrazolo[4,3-c]isoquinoline-5-yl)benzene-2,4-diol, and
4-(3-methyl-1H-pyrazolo[4,3-c]isoquinoline-5-yl)benzene-1,2-diol.

9. The method as claimed in claim 6, wherein the disease condition is osteoarthritis.

10. A pharmaceutical composition comprising a compound of the formula (I)

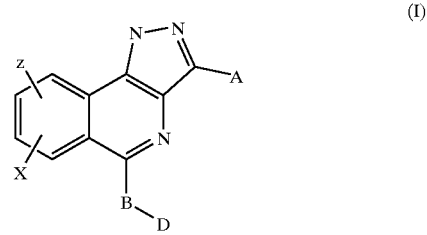

(I)

or a stereoisomeric form or a pharmaceutically acceptable salt of the compound of the formula I in combination with at least one pharmaceutically acceptable diluent, excipient a carrier, wherein
A is —($C_1$–$C_6$)-alkyl, in which alkyl is straight-chain or branched and is unsubstituted or optionally substituted, once or twice, independently of each other, by
—O—$R^1$ or
—C(O)—$OR^1$, in which $R^1$ is
hydrogen atom or
—($C_1$–$C_6$)-alkyl, —O—R1,
—C(O)—OR 1, or
heteroaryl having from 5 to 14 ring members, in which heteroaryl is unsubstituted or substituted once, twice or three times, independently of each other, by $R^2$, B is a covalent bond, or
—$(C_1$–$C_4)$-alkylene, in which alkylene is straight-chain or branched and is unsubstituted or optionally substituted, once or twice, independently of each other, by $R^1$, and $R^1$ is defined as above, D is heteroaryl having from 5 to 14 ring members, in which heteroaryl is unsubstituted or is substituted once, twice or three times, independently of each other, by $R^2$, in which $R^2$ is
hydrogen atom,
—$(C_1$–$C_4)$-alkyl,
—OH,
—O—$(C_1$–$C_4)$-alkyl,
halogen, or
—$N(R^3)$—$R^4$, in which $R^3$ and $R^4$ are, independently of each other, hydrogen atom or
—$(C_1$–$C_4)$-alkyl,
heterocycle having from 5 to 12 ring members, in which heterocycle is unsubstituted or substituted once, twice or three times, independently of each other, by $R^2$, and $R^2$ is defined as above,
—$(C_6$–$C_{14})$-aryl, in which aryl is substituted once, twice or three times, independently of each other, by
—OH,
—O—$(C_1$–$C_4)$-alkyl, or
—$N(R^3)$—$R^4$, in which $R^3$ and $R^4$ are, independently of each other, hydrogen atom or
—$(C_1$–$C_4)$-alkyl, or
—$(C_3$–$C_6)$-cycloalkyl, in which cycloalkyl is substituted, once, twice or three times, independently of each other, by
—$(C_1$–$C_4)$-alkyl,
—OH,
—O—$(C_1$–$C_4)$-alkyl,
halogen, or
—$N(R^3)$—$R^4$, in which $R^3$ and $R^4$ are, independently of each other, hydrogen atom or
—$(C_1$–$C_4)$-alkyl, and X and Z are identical or different and are, independently of each other,
hydrogen atom,
—$(C_1$–$C_4)$-alkyl,
—OH,
—O—$(C_1$–$C_4$-alkyl), or halogen.

11. The composition as claimed in claim 10, wherein
A is —$(C_1$–$C_3)$alkyl, in which alkyl is straight-chain or branched and is unsubstituted or optionally substituted, once or twice, independently of each other, by
—O—$R^1$, or
—C(O)—$OR^1$, in which $R^1$ is
hydrogen atom, or
—$(C_1$–$C_3)$-alkyl, or
—C(O)—$OR^1$, B is a covalent bond, D is phenyl, in which phenyl is unsubstituted or substituted, once, twice or three times, independently of each other, by $R^2$,
in which $R^2$ is
hydrogen atom,
—$(C_1$–$C_4)$-alkyl or
—$N(R^3)$—$R^4$, in which $R^3$ and $R^4$ are, independently of each other, hydrogen atom or
—$(C_1$–$C_3)$-alkyl,
pyridyl, in which pyridyl is unsubstituted or substituted, once, twice or three times, independently of each other, by $R^2$, and $R^2$ is defined as above, or
—$(C_4$–$C_6)$-cycloalkyl, in which cycloalkyl is unsubstituted or substituted, once, twice or three times, independently of each other, by $R^2$, and $R^2$ defined as above, and X and Z are identical or different and are, independently of each other, hydrogen atom or halogen.

12. The composition as claimed in claim 10, wherein the compound of the formula I is selected from the group consisting of:

5-(3-methoxyphenyl)-3-methyl-1H-pyrazolo[4,3-c]isoquinoline,
3-(3-methyl-1H-pyrazolo[4,3-c]isoquinoline-5-yl)phenol,
5-(2-methoxyphenyl)-3-methyl-1H-pyrazolo[4,3-c]isoquinoline,
5-(2,3-dimethoxyphenyl)-3-methyl-1H-pyrazolo[4,3-c]isoquinoline,
5-(2,4-dimethoxyphenyl)-3-methyl-1H-pyrazolo[4,3-c]isoquinoline,
5-(2,6-dimethoxyphenyl)-3-methyl-1H-pyrazolo[4,3-c]isoquinoline,
5-(3,4-dimethoxyphenyl)-3-methyl-1H-pyrazolo[4,3-c]isoquinoline,
5-(3,5-dimethoxyphenyl)-3-methyl-1H-pyrazolo[4,3-c]isoquinoline,
5-(2,3,4-trimethoxyphenyl)-3-methyl-1H-pyrazolo[4,3-c]isoquinoline,
5-(2,4,6-trimethoxyphenyl)-3-methyl-1H-pyrazolo[4,8-c]isoquinoline,
5-(3,4,5-trimethoxyphenyl)-3-methyl-1H-pyrazolo[4,3-c]isoquinoline,
5-(2-ethoxyphenyl)-3-methyl-1H-pyrazolo[4,3-c]isoquinoline,
5-(4-diethylaminophenyl)-3-methyl-1H-pyrazolo[4,3-c]isoquinoline,
3-methyl-5-pyridin-4-yl-1H-pyrazolo[4,3-c]isoquinoline,
3-methyl-5-pyridin-3-yl-1H-pyrazolo[4,3-c]isoquinoline,
3-methyl-5-pyridin-2-yl-1H-pyrazolo[4,3-c]isoquinoline,
3-methyl-5-(1-methylpiperidin-4-yl)-1H-pyrazolo[4,3-c]isoquinoline,
7,8-dimethoxy-5-(3-methoxyphenyl)-3-methyl-1H-pyrazolo[4,3-c]isoquinoline,
7,8-dimethoxy-3-methyl-5-pyridin-2-yl-1H-pyrazolo[4,3-c]isoquinoline,
7,8-dimethoxy-3-methyl-5-pyridin-3-yl-1H-pyrazolo[4,3-c]isoquinoline,
7-methoxy-5-(3-methoxyphenyl)-3-methyl-1H-pyrazolo[4,3-c]isoquinoline,
2-(3-methyl-1H-pyrazolo[4,3-c]isoquinolin-5-yl)phenol,
4-(3-methyl-1H-pyrazolo[4,3-c]isoquinolin-5-yl)benzene-2,4-diol, and
4-(3-methyl-1H-pyrazolo[4,3-c]isoquinolin-5-yl)benzene-1,2-diol.

13. A compound selected from the group consisting of:

3,5-diphenyl-1H-pyrazolo[4,3-c]isoquinoline,
5-benzyl-3-methyl-1H-pyrazolo[4,3-c]isoquinoline,
3-methyl-5-phenethyl-1H-pyrazolo[4,3-c]isoquinoline,
7,8-dimethoxy-3-methyl-5-phenyl-1H-pyrazolo[4,3-c]isoquinoline,
7-methoxy-3-methyl-5-phenyl-1H-pyrazolo[4,3-c]isoquinoline,
5-phenyl-1H-pyrazolo[4,3-c]isoquinoline-3-carboxylic acid, methyl 5-phenyl-1H-pyrazolo[4,3-c]isoquinoline-3-carboxylate, and (5-phenyl-1H-pyrazolo[4,3-c]isoquinolin-3-yl)methanol.

14. A pharmaceutical composition comprising one or more compounds as claimed in claim 13 in combination with at least one pharmaceutically acceptable diluent, excipient or a carrier.

15. A method of treating a disease condition selected from the group consisting of osteoarthritis, rheumatoid arthritis, asthma, rejection reactions on the part of the body against a transplanted organ or rejection reactions on the part of the transplanted organ against the body, comprising administering to a patient suffering from said disease condition a therapeutically effective amount of a compound as claimed in claim 13.

* * * * *